United States Patent
Gumlich et al.

(10) Patent No.: US 8,236,974 B2
(45) Date of Patent: Aug. 7, 2012

(54) PROCESS FOR PREPARING GLYCIDYL ESTERS

(75) Inventors: Kai Gumlich, Mannheim (DE); Joaquim Henrique Teles, Otterstadt (DE); Roland Merten, Weinheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/990,756

(22) PCT Filed: Jun. 10, 2009

(86) PCT No.: PCT/EP2009/057134
§ 371 (c)(1),
(2), (4) Date: Nov. 2, 2010

(87) PCT Pub. No.: WO2009/153194
PCT Pub. Date: Dec. 23, 2009

(65) Prior Publication Data
US 2011/0046401 A1   Feb. 24, 2011

(30) Foreign Application Priority Data
Jun. 18, 2008   (EP) .................................. 08158482

(51) Int. Cl.
*C07D 301/02*   (2006.01)
(52) U.S. Cl. ..................................................... 549/518
(58) Field of Classification Search .................. None
See application file for complete search history.

(56) References Cited

U.S. PATENT DOCUMENTS

| | | | |
|---|---|---|---|
| 2,856,413 A | 10/1958 | Malkemus et al. | |
| 4,069,234 A | 1/1978 | Wu | |
| 4,111,965 A | 9/1978 | Wu | |
| 4,257,966 A | 3/1981 | Wu | |
| 4,276,223 A | 6/1981 | Wu | |
| 4,892,954 A | 1/1990 | Brindoepke et al. | |
| 5,359,094 A * | 10/1994 | Teles et al. | 549/228 |
| 6,696,594 B2 * | 2/2004 | Au et al. | 560/210 |

FOREIGN PATENT DOCUMENTS

| | | |
|---|---|---|
| DE | 845 937 | 8/1952 |
| EP | 0 212 409 | 3/1987 |
| EP | 0 582 201 | 2/1994 |
| FR | 1 100 845 | 9/1955 |
| WO | 98 40371 | 9/1998 |

OTHER PUBLICATIONS

Clement and Cavell, Transition-Metal-Catalyzed Reactions Involving Imidazolium Salt/N-Heterocyclic Carbene Couples as Substrates, 43 Angew. Chem. Int. Ed. 3845-3847 (2004).*
U.S. Appl. No. 13/142,968, filed Jun. 30, 2011, Teles, et al.
International Search Report issued Aug. 4, 2009 in PCT/EP09/57134 filed Jun. 10, 2009.
U.S. Appl. No. 13/381,116, filed Dec. 28, 2011, Kunst, et al.

* cited by examiner

*Primary Examiner* — Janet Andres
*Assistant Examiner* — Timothy R Rozof
(74) *Attorney, Agent, or Firm* — Oblon, Spivak, McClelland, Maier & Neustadt, L.L.P.

(57) ABSTRACT

Process for preparing glycidyl esters, wherein carbonate esters of the formula I

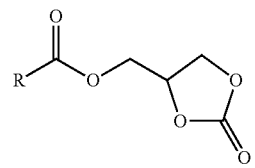

I are reacted in the presence of a homogeneous catalyst with elimination of carbon dioxide to form glycidyl esters of the formula II

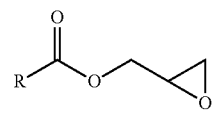

II where R in the above formulae is an organic radical having from 1 to 20 carbon atoms.

14 Claims, No Drawings

PROCESS FOR PREPARING GLYCIDYL ESTERS

The invention relates to a process for preparing glycidyl esters, in which carbonate esters of the formula I

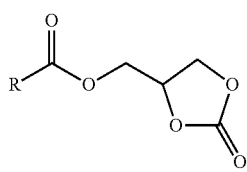

are reacted in the presence of a homogeneous catalyst with elimination of carbon dioxide to form glycidyl esters of the formula II

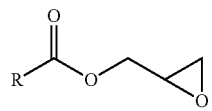

where R in the above formulae is an organic radical having from 1 to 20 carbon atoms.

Carbonate esters of the formula I require glycerol as starting material, and the importance of such carbonate esters therefore increases with the availability of glycerol.

Glycidyl compounds can be obtained from corresponding carbonate compounds by elimination of carbon dioxide. Such a process is described in WO 98/40371; the formulae indicated for suitable carbonate compounds also comprise esters (R=acyl). In WO 98/40371, a zeolite, i.e. a heterogeneous catalyst, is used as catalyst.

It is known from EP-A 582 201 and U.S. Pat. No. 2,856,413 that carbonate compounds can be converted into the corresponding glycidyl compounds, e.g. glyceryl carbonate into glycidol, in the presence of metal salts as catalysts at elevated temperatures (from 125 to 275° C.).

A good yield and high selectivity are fundamentally desired in such processes.

In addition, the process should be easy to carry out and the process products should be easy to separate off and free of by-products and/or catalysts. The catalysts should be able to be reused without a large outlay.

It was an object of the invention to provide such a process.

We have accordingly found the process defined at the outset.

In the process of the invention, carbonate esters of the formula I are reacted.

The radical R in formula I is an organic radical having from 1 to 20 carbon atoms, in particular from 1 to 15 carbon atoms. The organic radical can also comprise heteroatoms such as oxygen, nitrogen and sulfur.

R is preferably a hydrocarbon radical having from 1 to 20 carbon atoms, in particular from 1 to 15 carbon atoms.

It is particularly preferably an aliphatic hydrocarbon radical, in particular an alkyl group or alkenyl group.

As very particularly preferred radicals R, mention may be made of a C1-15-, in particular C6-C12-alkyl group and a C3-C10-alkenyl group, with these groups being able to be linear or branched.

Particular preference is given to the following carbonate esters of the formulae III and IV:

Formula III: carbonate ester of 2-ethylhexanoic acid

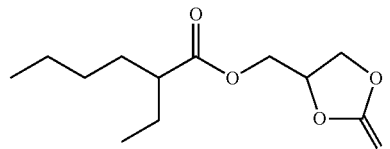

Formula IV: carbonate ester of methacrylic acid

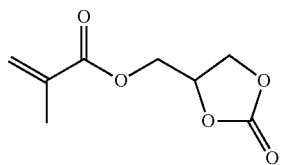

Furthermore, carbonate esters of 2-propylheptanoic acid, of neodecanoic acid and of isononanoic acid are of particular importance.

The process of the invention is carried out in the presence of a homogeneous catalyst.

For the present purposes, a homogeneous catalyst is a catalyst which dissolves at least partly in the starting materials or a solvent which is concomitantly used under the reaction conditions.

The homogeneous catalyst should preferably have a solubility in the starting material of the formula I or the solvent which is concomitantly used of at least 5 parts by weight, particularly preferably at least 20 parts by weight and very particularly preferably at least 50 parts by weight, in 100 parts by weight of starting material or solvent at 20° C., 1 bar.

The homogeneous catalyst is particularly preferably a salt. The salt can comprise organic or inorganic anions or cations.

The catalyst is particularly preferably an ionic liquid. For the purposes of the present invention, the term "ionic liquid" refers to a salt which is liquid at temperatures below 100° C., in particular at temperatures below 50° C. and particularly preferably at room temperature (21° C.). All data are based on atmospheric pressure (1 bar).

A salt having an organic cation is preferred as ionic liquid. The organic cation is, in particular, a heterocyclic ring system having at least one nitrogen atom, preferably 2 nitrogen atoms, as part of the ring system.

A suitable cation is, in particular, a pyridinium cation or an imidazolium cation.

The catalyst is very particularly preferably an imidazolium salt.

Possible imidazolium salts are, in particular, imidazolium salts of the formula V

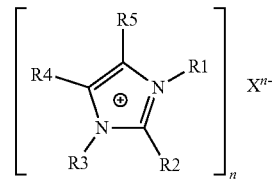

where
R1 and R3 are each, independently of one another, an organic radical having from 1 to 20 carbon atoms,
R2, R4, and R5 are each, independently of one another, an H atom or an organic radical having 1 to 20 carbon atoms,
X is an anion,
n is 1, 2 or 3.

Preference is given to R1 and R3 each being, independently of one another, an organic radical having from 1 to 10 carbon atoms. The organic radical can also comprise further heteroatoms, in particular oxygen atoms, for example hydroxyl groups, ether groups, ester groups or carbonyl groups.

In particular, R1 and R3 are each a hydrocarbon radical which can comprise, apart from carbon and hydrogen, at most hydroxyl groups, ether groups, ester groups or carbonyl groups.

Particular preference is given to R1 and R3 each being, independently of one another, a hydrocarbon radical which has from 1 to 20 carbon atoms, in particular from 1 to 10 carbon atoms, and comprises no other heteroatoms, e.g. oxygen or nitrogen. The hydrocarbon radical can be aliphatic (with unsaturated aliphatic groups also being included) or aromatic or comprise both aromatic and aliphatic groups. R1 and R2 are each preferably an aliphatic hydrocarbon radical.

As hydrocarbon radicals, mention may be made of, for example, the phenyl group, benzyl group, a phenyl group or benzyl group substituted by one or more C1-C4-alkyl groups, alkyl groups and alkenyl groups, in particular the allyl group. Very particular preference is given to R1 and R3 each being a C1-C10-alkyl group. As alkyl group, particular preference is given to a C1-C6-alkyl group, and in a particular embodiment the alkyl group is a C1-C4-alkyl group.

Very particular preference is given to R1 and R3 each being, independently of one another, a methyl, ethyl, n-propyl, isopropyl, n-butyl, sec-butyl or tert-butyl group, with the methyl, ethyl, n-propyl and n-butyl groups being of particular importance.

In a particular embodiment,
R1 and R3 are each a methyl group,
R1 and R3 are each an ethyl group,
R1 is a methyl group and R3 is an ethyl group,
R1 is a methyl group and R3 is an n-propyl group,
R1 is a methyl group and R3 is an n-butyl group.

R2, R4, and R5 are each, independently of one another, an H atom or an organic radical having from 1 to 20 carbon atoms, where R4 and R5 can also together form an aliphatic or aromatic ring. The organic radical can also comprise heteroatoms such as nitrogen or oxygen in addition to carbon and hydrogen; it can preferably comprise oxygen, especially in the form of hydroxyl groups, ester groups, ether groups or carbonyl groups.

In particular, R2, R4 and R5 are each, independently of one another, an H atom or a hydrocarbon radical which can comprise, apart from carbon and hydrogen, at most hydroxyl groups, ether groups, ester groups or carbonyl groups.

Preference is given to R2, R4 and R5 each being, independently of one another, a hydrogen atom or a hydrocarbon radical which has from 1 to 20 carbon atoms, in particular from 1 to 10 carbon atoms, and comprises no other heteroatoms, e.g. oxygen or nitrogen. The hydrocarbon radical can be aliphatic (with unsaturated aliphatic groups also being included) or aromatic or comprise both aromatic and aliphatic groups, where R4 and R5 can also form an aromatic or aliphatic hydrocarbon ring which may optionally be substituted by further aromatic or aliphatic hydrocarbon groups (the number of carbon atoms of the optionally substituted hydrocarbon ring including the substituents is preferably not more than 40, in particular not more than 20, particularly preferably not more than 15 or not more than 10).

Hydrocarbon radicals which may be mentioned are, for example, the phenyl group, a benzyl group, a phenyl group or benzyl group substituted by one or more C1-C4-alkyl groups, alkyl groups, alkenyl groups and, when R4 and R5 form a ring, an aromatic 5- or 6-membered ring formed by R4 and R5, a cyclohexene or cyclopentene ring, where these ring systems may, in particular, be substituted by one or more C1-C10-, in particular C1-C4-alkyl groups.

Aliphatic hydrocarbon radicals are preferred as hydrocarbon radicals.

Particular preference is given to R2, R4 and R5 each being, independently of one another, an H atom, a C1-C8-alkyl group or a C1-C8-alkenyl group, e.g. an allyl group.

Very particular preference is given to R2, R4 and R5 each being, independently of one another, an H atom, a methyl, ethyl, n-propyl, isopropyl, n-butyl, sec-butyl or tert-butyl group, with the methyl, ethyl, n-propyl and n-butyl groups being of particular importance.

In a particular embodiment, R2, R4 and R5 are each an H atom or a C1-C4-alkyl group; in particular, R2, R4 and R5 are each an H atom.

Specific cases of cations of the compounds of the formula I are:
1-Butyl-3-methylimidazolium (R1=butyl, R3=methyl)
1-Butyl-3-ethylimidazolium (R1=butyl, R3=ethyl)
1,3-Dimethylimidazolium (R1=methyl, R3=methyl)
1-Ethyl-3-methylimidazolium (R1=ethyl, R3=methyl)
1-Ethyl-2,3-dimethylimidazolium (R1=ethyl, R2=methyl, R3=methyl)

In formula V, n is 1, 2 or 3; the anion correspondingly has one, two or three negative charges and one, two or three imidazolium cations are correspondingly present in the salt.

n is preferably 1 or 2, particularly preferably 1; the anion is therefore particularly preferably monovalent.

In formula V, X is an anion. Suitable anions are organic and inorganic anions which together with the cation give an ionic liquid. Anions which may be mentioned are, in particular, halides, pseudohalides such as $CN^-$, $SCN^-$, $OCN^-$, sulfates, phosphates, anions having organic groups, in particular alkyl esters, e.g. phosphonates or sulfonates.

For the purposes of the present invention, chloride is preferably not used as anion since the presence of chlorine or chlorides is undesirable for some uses of the compounds.

The homogeneous catalyst therefore preferably does not comprise any chlorine or chloride. The catalyst is preferably a chlorine-free catalyst.

Particular preference is generally given to an iodide as anion. The homogeneous catalyst is therefore preferably an iodide.

Particular preference is given to an imidazolium iodide, in particular an imidazolium iodide of the above imidazolium cations.

The amount of homogeneous catalyst is preferably from 0.1 to 50 parts by weight, particularly preferably from 0.5 to 40 parts by weight, per 100 parts by weight of starting material of the formula I. In particular, the homogeneous catalyst is used in amounts of at least 0.1 part by weight, in particular 0.5 part by weight; the amount is generally not greater than 20 parts by weight or in particular not greater than 10 parts by weight, based on 100 parts by weight of the starting material of the formula I.

In the process of the invention, it is possible, if desired, to use additional solvent. The addition of solvent can, in particular, be helpful for process engineering reasons, e.g. to take up heat.

The homogeneous catalyst can, if desired, also be dissolved in the solvent rather than in the starting material. In the case of an ionic liquid as catalyst, the ionic liquid can assume the functions of a solvent. If the ionic liquid is used in only small amounts, the concomitant use of solvents may also be advantageous here.

Possible solvents are ones which are liquid under the reaction conditions and do not react with the epoxy group (glycidyl ring) formed. These are, for example, polyethers whose terminal hydroxy groups are etherified with alkyl groups; such polyethers are commercially available, for example, under the name Plurafac®. The solvent is preferably at least partly miscible with the starting material and is particularly preferably miscible in any amounts with the starting material.

The process can be carried out batchwise, semicontinuously or continuously.

The temperatures are preferably in the range from 100 to 275° C., in particular from 120 to 200° C.

The reaction is preferably carried out under reduced pressure, and the glycidyl ester obtained is preferably distilled off from the reaction mixture directly under reduced pressure.

The products obtained have a glycidyl ring in place of the carbonate ring.

The carbonate of the formula III gives the glycidyl ester of the formula VI:

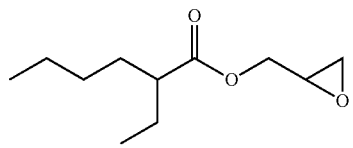

The carbonate of the formula IV gives the glycidyl ester of the formula VII:

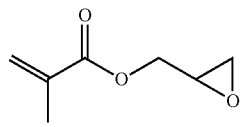

The glycidyl esters can be prepared in a simple manner by the process of the invention. High yields and selectivities are achieved.

The process of the invention is also of particular importance for glycerol as raw material.

Glyceryl monoesters can be obtained in a simple manner by reacting glycerol with carboxylic acids. The glyceryl monoesters can be converted by reaction with $CO_2$ or dialkyl carbonates such as dimethyl carbonate or diethyl carbonate into the compounds of the formula I and then converted in a simple manner by means of the process of the invention into the glycidyl esters of the formula II.

EXAMPLES

Apart from the 2-ethylhexanoic acid ester of glycerol carbonate (2-EHGCE) the corresponding methacrylic ester (MAAGCE) was also used as starting material.

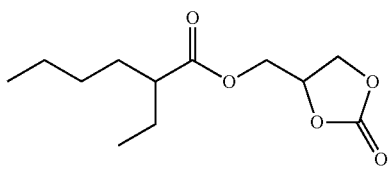

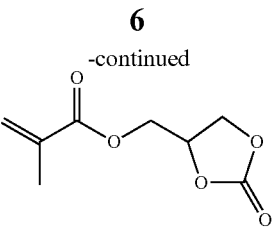

The following catalysts were used:
NaI CaF Butylmethylimidazolium iodide (BMIM iodide)
KI $Na_2SO_4$
$Li_2CO_3$ $Li_3PO_4$ The experiments were carried out in two variants:
a) Batch experiments: Both the carbonate and the catalyst were placed together in the still pot of a distillation apparatus. The mixture was subsequently heated under reduced pressure and the glycidyl ester distilled over.
b) Semibatch experiments: For these experiments, only the catalyst and an inert solvent were placed in the still pot (in the case of the ILs, part of the solvent was omitted). The carbonate was continuously added dropwise as soon as the still pot had reached the required pressures and temperatures.

Batch Experiments

Example No. 1

Glycidyl 2-ethylhexanoate by Elimination of $CO_2$ Using NaI as Catalyst (Comparative Experiment, NaI is Suspended in the Starting Material)

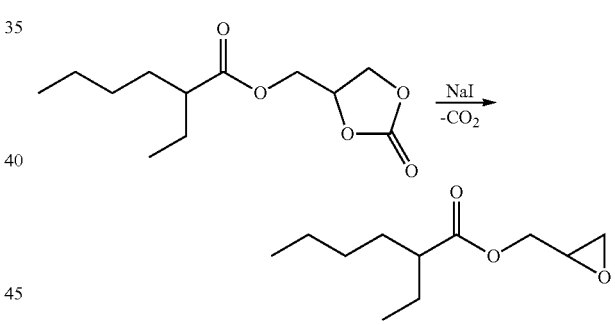

Apparatus
250 ml four-neck flask Magnetic stirrer Capillary for bubbling in $N_2$
Thermometer 25 cm Vigreux column
Dropping funnel Distillation attachment+multineck receiver

| Batch | MW [g/mol] | Molar amount [mmol] | Mass [g] | Volume [ml] |
|---|---|---|---|---|
| 2-Oxo-[1,3]dioxolan-4-ylmethyl 2-ethylhexanoate | 244.29 | 409 | 100 | |
| NaI | 149.89 | 46.7 | 7 | |

Process Step
　　Place carbonate ester and NaI in flask
　　Commence bubbling-in of $N_2$ via capillary
　　Evacuate to 100 mbar
　　Heat to 180° C.

Reduce pressure to 11 mbar
The product distills over at a temperature at the bottom of about 180-189° C. and a temperature at the top of 110-114° C.
Yield: 79%
Epoxide equivalents: 222 g/eq
Water content: <0.01 g/100 g
Color number: 36 APHA
Semibatch Experiments Example 11

Glycidyl 2-ethylhexanoate by Elimination of $CO_2$ Using BMIM Iodide as Catalyst in Plurafac LF 431

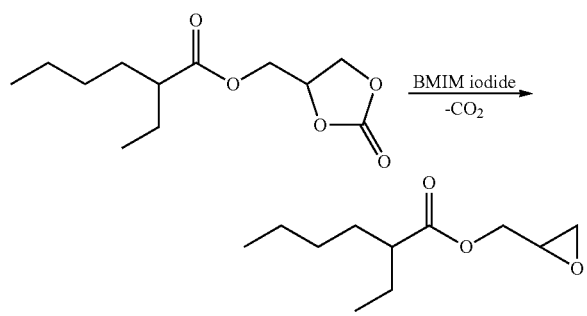

Apparatus
250 ml four-neck flask Magnetic stirrer Capillary for bubbling in $N_2$
Thermometer 25 cm Vigreux column
Dropping funnel Distillation attachment+multineck receiver

| Batch | MW [g/mol] | Molar amount [mmol] | Mass [g] | Volume [ml] |
|---|---|---|---|---|
| 2-Oxo-[1,3]dioxolan-4-ylmethyl 2-ethylhexanoate | 244.29 | 327 | 80 | |
| BMIM iodide | 266.13 | 3 | 0.8 | |
| Plurafac LF 431 | | | | 25 |

Process Step
Place carbonate ester together with BMIM iodide and Plurafac LF431 in flask
Evacuate to 1 mbar
Heat to 155° C.
Add ester dropwise over a period of 45 h
The product distills over at a temperature at the bottom of about 154-200° C. and a temperature at the top of 97-98° C.
Yield: 82%

TABLE 1

Overview of experiments

| Experiment No. | Starting material | Amount [g] | Catalyst | Amount based on starting material [%] by wt. | Solv. | Yield [%] |
|---|---|---|---|---|---|---|
| 1 | 2-EHGCE | 100 | NaI | 7 | — | 79 |
| 2 | 2-EHGCE | 71.6 | $Na_2SO_4$ | 7 | — | 0.3 |
| 3 | MAAGCE | 135.7 | KI | 7 | — | 2 |
| 4 | 2-EHGCE | 51.2 | $Li_2CO_3$ | 7 | — | 0 |
| 5 | 2-EHGCE | 40.7 | CaF | 7 | — | 0 |
| 6 | 2-EHGCE | 36.2 | KI | 7 | — | 23 |
| 7 | 2-EHGCE | 90 | $Li_3PO_4$ | 7 | — | 5.6 |
| 8 | 2-EHGCE | 73.8 | BMIM iodide | 11.3 | — | 98 |
| 9 | 2-EHGCE | 80 | BMIM iodide | 10 | — | 90 |
| 10 | 2-EHGCE | 80 | BMIM iodide | 31.3 | — | 81 |
| 11 | 2-EHGCE | 80 | BMIM iodide | 1 | Plurafac LF 431 | 82 |
| 12 | MAAGCE | 80 | BMIM iodide | 31.3 | — | 8.6 |
| 13 | MAAGCE | 80 | BMIM iodide | 31.3 | — | 3.5 |
| 14 | 2-EHGCE | 80 | BMIM iodide | 7 | — | 79 |

Experiments 10, 11, 12 and 13 were carried out in semibatch mode.
The other experiments were carried out in batch mode.
Experiments 1 to 7 are comparative experiments in which the salt was suspended in the starting material.

The invention claimed is:
1. A process for preparing a glycidyl ester, comprising:
reacting a carbonate ester represented by formula I

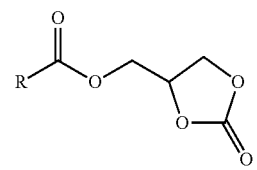

in the presence of a homogeneous catalyst; and
eliminating carbon dioxide to form a glycidyl ester represented by formula II

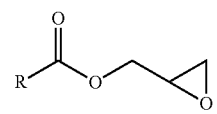

where R in the formula I and the formula II is an organic radical having from 1 to 20 carbon atoms,
wherein the homogeneous catalyst is a salt which is an ionic liquid at a temperature of less than 100° C. at 1 bar.
2. The process according to claim 1, wherein R is a hydrocarbon radical.
3. The process according to claim 1, wherein R is a C1-C20-alkyl group.
4. The process according to claim 1, wherein the homogeneous catalyst has a solubility in the carbonate ester of the formula I or in a solvent of at least 5 parts by weight in 100 parts by weight of the carbonate ester or the solvent at 20° C., 1 bar.

5. The process according to claim 1, wherein the ionic liquid copmrises an imidazolium salt.

6. The process according to claim 1, wherein the the ionic liquid comprises an iodide.

7. The process according to claim 1, wherein the the ionic liquid comprises an imidazolium iodide.

8. The process according to claim 1, wherein the homogeneous catalyst is present in an amount of from 0.1 to 50 parts by weight per 100 parts by weight of the carbonate ester of the formula I.

9. The process according to claim 1, further comprising:

reacting a carboxylic acid and glycerol to obtain a glyceryl monoester; and converting the glyceryl monoester into the carbonate ester of the formula I.

10. The process according to claim 1, wherein the homogeneous catalyst is present in an amount of from 0.5 to 10 parts by weight per 100 parts by weight of the carbonate ester of the formula I.

11. The process according to claim 1, wherein the ionic liquid comprises at least one imidazolium salt represented by formula V:

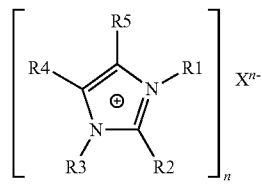

where R1 and R3 are each, independently of one another, an organic radical having from 1 to 20 carbon atoms, R2, R4, and R5 are each, independently of one another, a hydrogen atom or an organic radical having 1 to 20 carbon atoms, X is an anion, and n is 1, 2 or 3.

12. The process according to claim 11, wherein in the formula V, R1 and R3 are each independently of one another a methyl, ethyl, n-propyl, isopropyl, n-butyl, sec-butyl or tert-butyl group.

13. The process according to claim 11, wherein in the formula V, R2, R4 and R5 are each independently of one another a hydrogen atom or a methyl, ethyl, n-propyl, isopropyl, n-butyl, sec-butyl or tert-butyl group.

14. The process according to claim 11, wherein the at least one imidazolium salt is butylmethylimidazolium iodide.

* * * * *